United States Patent [19]

Sulc

[11] Patent Number: 5,195,891
[45] Date of Patent: Mar. 23, 1993

[54] ADJUSTABLE DENTAL IMPLANT SYSTEM

[76] Inventor: Josef M. Sulc, 1145 Mountain Rd., Wilton, Conn. 06897

[21] Appl. No.: 623,135

[22] Filed: Dec. 6, 1990

[51] Int. Cl.[5] ............................................. A61C 8/00
[52] U.S. Cl. .................................... 433/173; 433/174
[58] Field of Search ............... 433/169, 181, 173, 174, 433/175, 176

[56] References Cited

U.S. PATENT DOCUMENTS

| | | | |
|---|---|---|---|
| 3,656,236 | 4/1972 | Kurer | 433/174 |
| 4,488,875 | 12/1984 | Niznick | 433/173 |
| 4,540,367 | 9/1985 | Sulc | 433/181 |
| 4,645,453 | 2/1987 | Niznick | 433/173 |
| 4,713,004 | 12/1987 | Linkow et al. | 433/174 |
| 4,738,623 | 4/1988 | Driskell | 433/173 |
| 4,780,080 | 10/1988 | Haris | 433/173 |
| 4,793,808 | 12/1988 | Kirsch | 433/173 |
| 4,832,601 | 5/1989 | Linden | 433/173 |
| 4,854,872 | 8/1989 | Detsch | 433/173 |
| 4,907,969 | 3/1990 | Ward | 433/173 |
| 4,932,868 | 6/1990 | Linkow et al. | 433/174 |
| 4,934,935 | 6/1990 | Edwards | 433/174 |
| 4,957,438 | 9/1990 | Box | 433/181 X |
| 4,988,297 | 1/1991 | Lazzara et al. | 433/173 |
| 5,007,835 | 4/1991 | Valen | 433/174 |
| 5,030,095 | 7/1991 | Niznick | 433/173 |
| 5,071,350 | 12/1991 | Niznick | 433/173 |

FOREIGN PATENT DOCUMENTS

3406448 8/1984 Fed. Rep. of Germany ...... 433/174

Primary Examiner—Robert P. Swiatek
Assistant Examiner—Nicholas D. Lucchesi
Attorney, Agent, or Firm—Pennie & Edmonds

[57] ABSTRACT

The present invention relates to an endosteal implant system and a method for mounting a dental prosthesis on one or more implants. The system comprises an implant, a two-piece anchor whereby one piece is an angled support for mounting a dental prosthesis and the second piece is a threaded base portion for securing to the implant. The support is seated within the base portion and is rotatable about the longitudinal axis of the base portion. The alignment is achieved by first threading in the base portion into the implant and rotating the support until a best alignment is made. An accurate visual intra-oral evaluation of the anchor alignment is made utilizing a unique alignment handle which is snapped into each support. If the alignment is not satisfactory, the support with the alignment handle can be rotated until a satisfactory alignment is achieved. If a satisfactory alignment is not visually indicated, differently angled prosthetic supports may be used in various bases to achieve a satisfactory alignment of all supports. When a satisfactory alignment is achieved, the base and the support are marked to capture the aligned orientation. The base portion is removed from the implant and then the support is bonded to the base portion using the mark to correctly align the support in relation to the base portion. The anchor is again threaded into the implant. Because of the precise nature of the threading, the anchor will align as marked when completely threaded into the implant. The dental prosthesis can be then attached to the anchor.

32 Claims, 4 Drawing Sheets

ADJUSTABLE DENTAL IMPLANT SYSTEM

BACKGROUND OF THE INVENTION

1. Field of the Invention

The present invention relates to an endosteal implant assembly and more particularly, to a novel abutment-/anchor, hereinafter referred to as anchor, for adjustably supporting one or more prosthetic teeth or appliances at a desirable orientation relative to the path of insertion of the restoration. The present invention is particularly suited, but not limited, to use with patient-removable restorations.

2. Background of the Prior Invention

A dental prosthesis for replacing one or more missing teeth may be accomplished by placement of one or more dental implants in the jawbone and corresponding number of anchors to which the dental prosthesis is secured thereto. The anchor is normally screwed or bonded into the implant. The implant is generally made from a titanium alloy or other rigid materials which are non-reactive with human tissue or fluid.

It is well known that the angle of a dental anchor must be aligned with the intended angle of the path of insertion of the restoration and must be maintained from abutment to abutment, in cases where multiple implants are employed, to facilitate a smooth and non-traumatic insertion and function of a removable or a fixed appliance. The determination of the most desirable path of insertion of the appliance may be governed by factors such as the position of adjacent natural teeth, arc of closure, ridge contour and the patient's dexterity. Prior inventions for adjustably aligning the prosthetic tooth are disclosed, for example, in U.S. Pat. No. 4,713,004 to Linkow et al, U.S. Pat. No. 4,738,623 to Driskell, U.S. Pat. No. 4,780,080 to Haris, U.S. Pat. No. 4,832,601 to Linden, U.S. Pat. No. 4,854,872 to Detsch, U.S. Pat. No. 4,907,969 to Ward, U.S. Pat. No. 4,932,868 to Linkow et al, and U.S. Pat. No. 4,934,935 to Edwards.

Specifically, it is well known in the present field to place a dental implant in the jawbone, whereby through the process of osseointegration the bone grows closely around the implant, permanently integrating the implant into the jawbone. Various attempts have been made in the past to properly align the dental anchor in relation to the path of insertion with an improperly aligned dental implant so that a prosthetic tooth, which is to be formed on the dental anchor, properly aligns with the neighboring teeth. One example of the prior technique is disclosed in U.S. Pat. No. 4,713,004 to Linkow et al (Linkow). In this example, an implant is placed in the bone and one end of an angled threaded shaft is threaded into the implant and rotated into a proper orientation. A wedge shaped collar having an angled upper surface is placed around the angled shaft and the upper surface is positioned to coincide with the angle of the shaft so that the free end of the shaft extends perpendicularly from the angled surface. A prosthetic tooth anchor is threaded on the free end of the shaft to secure the collar in a set orientation. Linkow also discloses an alternative embodiment of aligning a prosthetic tooth, in which, instead of the angled shaft and collar, an intermediary anchor having a ball and socket joint is threaded in the implant. A bolt, which is attached to a prosthetic tooth anchor, is screwed completely through the ball to fix the position of the ball relative to the socket once an alignment has been accomplished.

Another technique employed in the prior art is disclosed in U.S. Pat. No. 4,780,080 to Haris. Haris places a conventional dental implant in the jawbone, and also secures an intermediary anchor to the implant. To correct the improper orientation of the implant and the anchor, an asymmetrically shaped frusto-conical prosthetic tooth anchor is positioned coextensively with the intermediary anchor. By rotating the asymmetrically shaped anchor about the longitudinal axis of the implant, various alignments can be achieved. Once a proper setting is identified, the frusto-conically shaped anchor is bonded to the intermediary anchor while the intermediary anchor is still permanently secured to the implant.

Yet another technique employed in prior art is disclosed in U.S. Pat. No. 4,832,601 to Linden. Linden utilizes a hexagonally-shaped intermediary anchor which is fastened to a complementary hexagonal bore formed in a dental implant. A prosthetic tooth anchor is adjustably secured to the intermediary anchor with a screw. The intermediary and the prosthetic tooth anchors function much like a ball and socket joint when the screw is loosened. That is, the prosthetic tooth anchor may move universally within the intermediary anchor. Once a proper alignment is made, the intermediary anchor and the prosthetic anchor may then be entirely removed from the implant. The screw is then tightened to immobilize the prosthetic support anchor relative to the intermediary anchor. The prosthetic support anchor with a prosthetic tooth formed thereon and the intermediary anchor is then placed back into the implant and secured thereto by a conventional means such as bonding or by a mechanical means.

Finally, U.S. Pat. No. 4,934,935 to Edwards also employs a conventional implant technique for setting an implant in the jawbone. An intermediary anchor is temporarily plugged into the implant and is properly positioned therein by rotating the anchor which is set at a predetermined angle. The anchor is then bonded to the implant once properly positioned. A prosthetic tooth anchor is then screwed into the angled intermediary anchor for supporting a prosthetic tooth thereon.

While these prior inventions make provisions for aligning a prosthetic tooth with the neighboring teeth, there are numerous disadvantages. These would include extreme complexity, to a point of impossible execution in actual clinical situations; limited application, suited only to fixed, permanently cemented restorations such as bridges or single crowns; not applicable to patient-removable restorations; the necessity of screw access holes on the chewing surfaces of the artificial teeth (described as "Swiss Cheese" effect in recent literature); and limited serviceability and retrievability of abutments or anchors. In short, the prior inventions do not present a simple, practical method for independent alignment of implant supported retrievable anchors for patient-removable restorations.

SUMMARY OF THE INVENTION

Recently, the use of dental implants has seen a tremendous growth. The technique of placement of the implants into the jawbone has been refined and the success rate has been excellent. For people with no teeth or roots of teeth left, the implants represent an exciting treatment option. The present invention was devised with the intention to simplify and make more effective the procedures for the operator and to further increase the success rate for the patients. Specifically, because of a simple bonding method and a unique two component adjustable anchor with alignment handles, it is now possible to provide patients with accurately aligned, simple, economical and extremely effective anchors as a means for removably retaining implant supported restorations. With the present invention the implant does not have to be exactly placed and/or aligned with the desired path of insertion of the dental appliance since the anchor can be independently adjusted to facilitate the alignment. Additionally, the anchor has been formed so that a dental prothesis may be taken completely off the anchor and placed back on the anchor by the user.

The present invention comprises an implant utilizing a conventional osseointegration technique for firmly anchoring the implant in the jawbone and a two-piece anchor. One piece is configured as a dental prosthesis support for removably supporting one or more prosthetic teeth and a second piece is configured as a threaded base portion for semi-permanently attaching to the implant. More specifically, the support is removably and adjustably situated within the threaded base portion so that the support is rotatable within the threaded base portion about the longitudinal axis of the threaded base portion. The support has an upper protrusion that is angled with respect to a lower portion thereof. By rotating the support with respect to the threaded base portion, a plurality of alignments can be achieved. The support comes with various preselected angles so that various alignments can be realized using various selections of the pre-angled supports. In addition, unique alignment handles are employed to facilitate an intra-oral assessment of functional alignment between two or more anchors. The handles also simplify the insertion of the implant assembly into the implant by providing an extension surface for easy grasping and handling of the assembly. The handles may be used either to carry the support with its base snapped onto it to the implant in the mouth, or the support alone to the base already situated in the implant.

In carrying out the installation of the implant and the anchor, one or more implants are initially strategically placed in the jawbone. After the implants are fully integrated, i.e, after the jawbone completely grows around the implants, a base portion with or without a prosthetic support and alignment handle seated therein is threaded into each implant and fully tightened thereto. If a prosthetic support of a desired angle and an alignment handle have not been previously seated in each base, an alignment handle is snapped into each angled prosthetic support and the alignment handle with the angled prosthetic support is then seated in each base portion. Each prosthetic support with its alignment handle is rotated about the longitudinal axis of the base until the best alignment is achieved. If a visual assessment of mutual alignment of the handles snapped in the anchors does not indicate a satisfactory alignment even if the supports are adjusted, a differently angled prosthetic support may be used in various bases to achieve a satisfactory alignment of all anchors.

When the best alignment is achieved, the alignment of the support with respect to the base is marked so as to capture the desired orientation. Following marking and removal from the implant, the support is then separated from the base portion. The base portion and the support are cleaned and bonded utilizing a conventional bonding technique, with the support being aligned with respect to the base portion using the mark to properly orient the support. Once the bond is set, the support and the threaded base portion, now as one piece, is ready to be threaded back into the implant. The threads of the base are coated with a medical grade silicone adhesive to seal the threads from oral fluids to eliminate bacterial growth and to prevent the anchor from loosening from the implant. The adhesive properties of this type of silicone material are such that it is possible to allow deliberate unthreading of the anchor from the implant if replacement is required. When the anchor is completely threaded into the implant, the precision threading assures that the anchor will be returned to the exact same position as during the marking step.

Since the bonding takes place completely outside the patient's mouth, the procedure is easy to accomplish. In addition, since the properly oriented base portion and support are bonded outside the mouth, the bonding takes place in a dry environment and the strength of the bond is thus not affected by the saliva of the patient. Moreover, in the present invention, the support comprises a female eyelet, similar to the type disclosed in U.S. Pat. No. 4,540,367, whereby a dental prothesis having one or more prosthetic teeth is removably attached to one or more female eyelets. In particular, the prosthesis has one or more nylon male caps embedded thereto, each male cap seating on one of the female eyelets, as disclosed in U.S. Pat. No. 4,540,367. Thus, the metal female eyelet of the anchor is protected from wear by the nylon-to-metal contact of the snap-in nylon male. However, should the female eyelet or any other portion of the anchor suffer any wear or damage, it can be readily replaced with a new anchor by simply removing the dental prosthesis and unscrewing the anchor from the implant. The new anchor is aligned using the alignment technique as described above.

Accordingly, the object of the invention is to provide a simple and yet effective means and a method for aligning anchors of an endosteal implant.

Another object of the invention is to provide an anchor that is readily removable and replaceable with respect to the endosteal implant.

Another object of the invention is to provide a dental prosthesis that is readily removable and reattachable to one or more anchors of the corresponding number of endosteal implants.

Still another object of the invention is to enable the bonding of a prosthetic support to the base support in a dry environment.

The foregoing and other features of the present invention will become readily apparent hereafter from the following description:

DETAILED DESCRIPTION OF THE INVENTION

Figure 1:
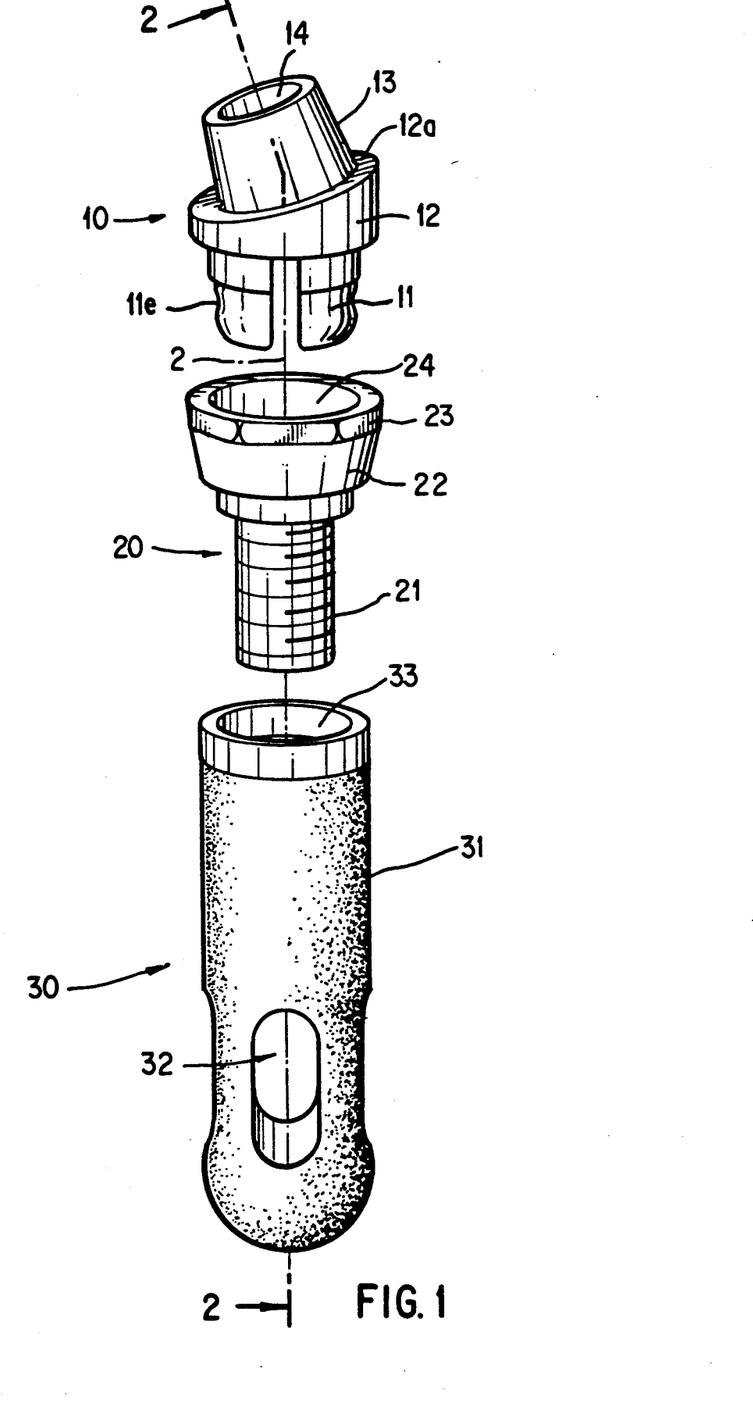
FIG. 1 is a perspective view of the present dental implant unit in unassembled form.

FIG. 1 shows a dental implant unit in unassembled form. The dental implant comprises an implant 30 and an anchor having a base 20 and an angled support 10. The implant has an elongated body 31, which is preferably made of a titanium alloy or other suitable materials which do not react with human tissue or fluid. Openings 32 are formed in the lower portion of the implant. A threaded cavity 33 is formed from the upper end of the implant for attaching the base. The purpose of the openings 32 is for the jawbone to grow thereinto and form a strong bond therewith. The base includes a threaded shaft 21 for mating with the threaded cavity 33 and an upper body 22 with flattened surfaces 23. The flattened surfaces form a gripping area for an appropriate tool i.e., during tightening against or loosening the base from the implant. The upper body forms a cavity 24 for providing a snap fit retention with a slotted lower projection 11 of the angled support 10. Specifically, a convex profiled waist 11e and a complementary surface profile formed in the cavity 24 permits the slotted lower projection to retain therein while permitting a rotational movement about a longitudinal axis 2 of the implant assembly.

The angled support comprises a wedge shaped intermediary body 12 with an angled upper surface 12a. The slotted lower projection 11, which has an hourglass profile, extends perpendicularly from a lower surface of the body 12 and an upper angled female eyelet 13 extends perpendicularly from the angled surface 12a. The female eyelet 13 is slightly tapered toward the uppermost surface thereof to form a truncated conical seat, with an opening 14 formed therein for seating a male cap 40. The detailed description of the female eyelet follows below in conjunction with the description of the male cap 40.

Figure 2:
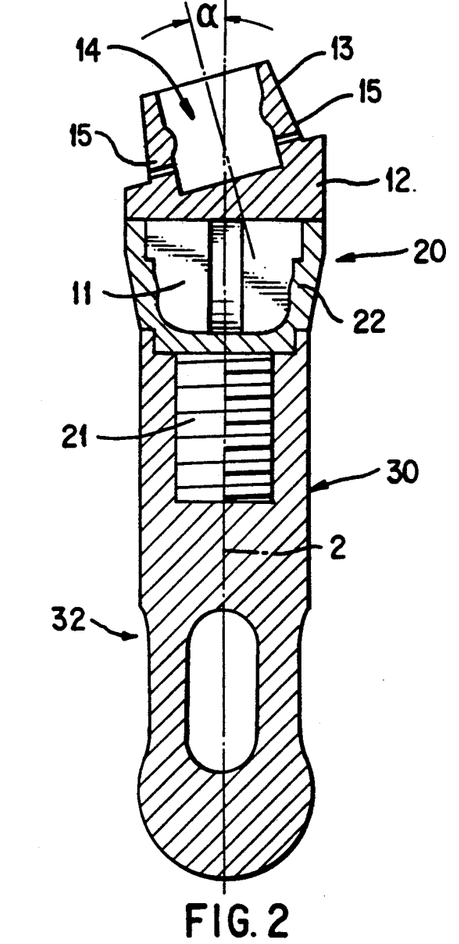
FIG. 2 is a cross sectional view taken along the line 2—2 of FIG. 1, with the dental assembly unit in assembled form.

FIG. 2 illustrates a cross sectional view taken along the line 2—2 of FIG. 1, with the implant unit 1 in assembled form. A pair of holes 15, set at 180° apart, is formed on the female eyelet 13 to permit drainage of saliva should saliva enter through the opening 14 of the female eyelet. Note that the female eyelet is angled at α° relative to the longitudinal axis 2 of the implant.

Figure 3:
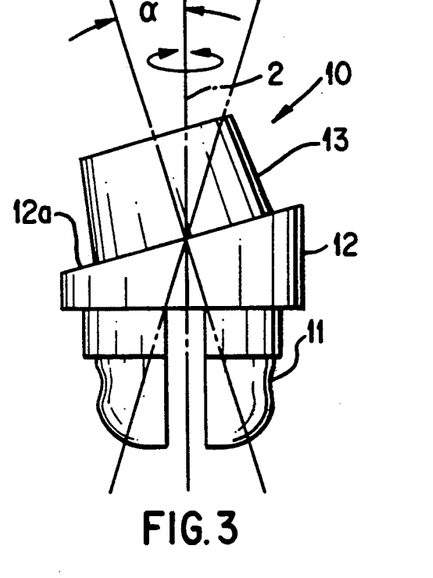
FIG. 3 is a front view of the angled support for mounting a dental prothesis thereto.

FIG. 3 shows a side elevational view of the support 10. The female eyelet is shown at an angle α relative to the longitudinal axis of the implant unit. The angle α is fixed, and the support 10 with differently angled female eyelet is used when different angles are needed. The female eyelet is preferably formed with angle α at 5°, 11°, and 17° relative to the longitudinal axis 2. It is to be noted that, due to the angling of the female eyelet, by rotating the support 10 about the longitudinal axis 2 of the base 20, various offset positions about the 360° of the axis 2 can be achieved.

Figure 4:
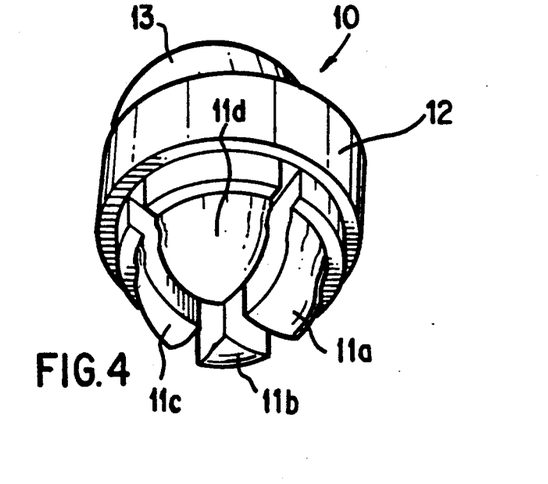
FIG. 4 is a perspective view of the angled support, showing the slotted lower portion thereof.

FIG. 4 illustrates the lower projection 11 of the support 12, which conforms to the hourglass shape of the cavity 24 formed within the base 20. In particular, the lower projection 11 extends downwardly from the body 12 and the projection has a pair of slots which intersect at a right angle, with the slots extending in the direction of the projection. Accordingly, four identically shaped prongs 11a, 11b 11c, 11d are formed. The slots enable the prongs to move resiliently in the radial direction which is perpendicular to the direction of the projection when inserted or seated in the cavity 24 of the base 20. The convex profiled waist 11e and the complementary profile surface formed in the cavity 24 and the cross-slots of the projection permit a light snap fit retention with the base while permitting the support 10 to rotate about the longitudinal axis 2. In addition, the cuts also provide space for the adhesive to fill during the bonding stage so that a strong bond is formed between the support 10 and the base anchor 20.

Figure 5:
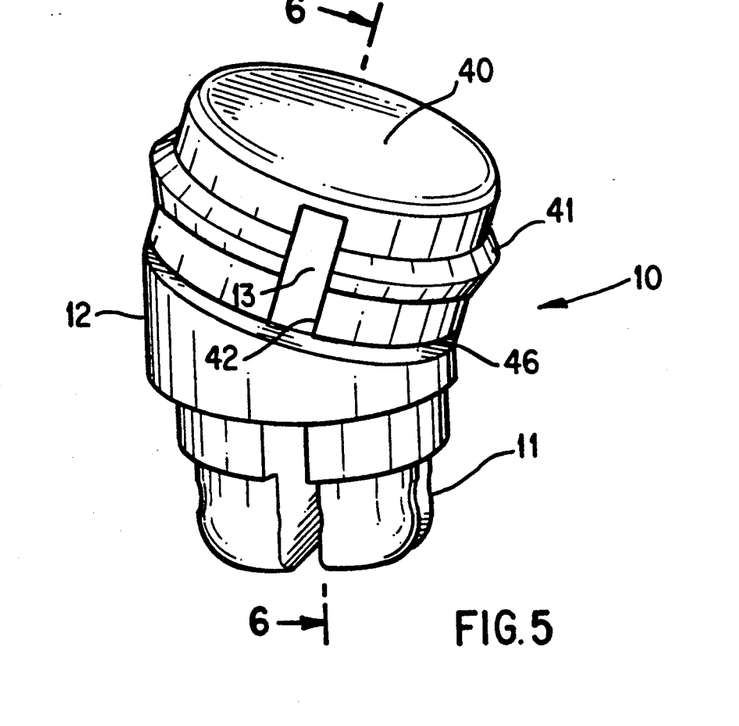
FIG. 5 is a perspective view of the angled support with a removable nylon cap placed on the upper portion thereof.
Figure 6:
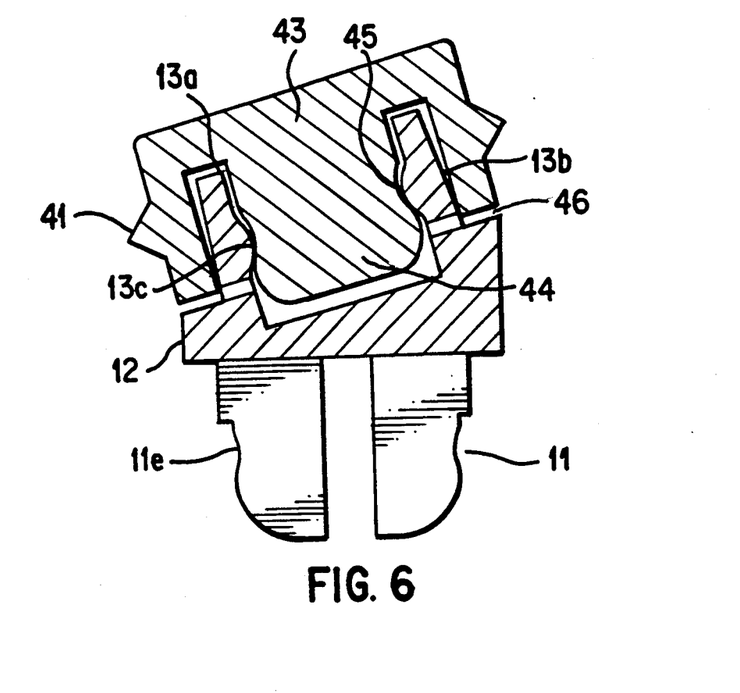
FIG. 6 is a front elevational cross-sectional view taken along the line 6—6 of FIG. 5.

FIGS. 5 and 6 show a male prothesis retention cap 40 placed over the female eyelet 13. In particular, the female eyelet takes a form of a cup having a substantially cylindrical upstanding side wall 13b. The outer surface of the side wall of the socket generally is slightly tapered in outline toward the uppermost surface 13a thereof. The inner surface of the side wall is contoured to form a necked-down region or constriction 13c in a form of a convex arc shaped profile. The female eyelet 13 is preferably formed of titanium or other metallic material which conventionally finds use in the field of dentistry.

The male cap 40 preferably is formed of a plastic material having sufficient strength and durability to permit repeated connection and disconnection with the female eyelet. The material of the male cap should also provide a measure of resilience to permit a snap fit retention with the female eyelet. In addition, the material of the male cap should develop a retaining friction between the male cap and the female eyelet to retain the male cap and a dental prothesis, which is formed around the male cap, in a positive manner, while permitting removal and reinsertion of the male cap with the dental prothesis when desired. The male cap, accordingly, may be formed of strong nylon, a material that also has been found to eliminate problems of wear of the female eyelet. In this connection, the male cap will absorb all wear, and as wear increases, the male cap is replaceable with a new male cap. The replacement technique whereby one male member is replaced by another is disclosed in U.S. Pat. No. 4,540,367 and in a copending application Ser. No. 07/578,396, filed Sep. 7, 1990, which are incorporated herein by reference.

The male cap 40 is also characterized by a substantially cup-shaped structure. As such, the male cap includes a wall 42 which extends from a base 43. In addition, a projection 44 extends from the base, along the axis of the wall 42 and has an outer contour which generally is complementary to that of the inner surface 13c of the side wall 13b of the female eyelet. Specifically, the outer contour is substantially shaped in the form of an hourglass. The projection includes a constriction at about the midpoint of its length, where two convex curve profiles meet, forming a waist portion 45. The waist allows a snap fit retention in the female eyelet and permits a substantial universal movement capability of the dental prothesis which is attached to outer surfaces of the male cap.

A ridge 41 is formed around the outer perimeter thereof and a dental prothesis is formed around the outer surface of the male cap, with the ridge securely holding the cap in the dental prothesis. A gap is formed between the upper most surface 13a and the underside of the base 43 and another gap 46 is formed between the upper inclined surface 12a and the lowermost side of the male cap to enable the male member to move along the direction of the projection when force is applied to the dental prothesis formed therearound. A greater detailed description of the manner in which a dental prothesis is secured to the male cap and the manner in which the male cap resiliently moves along the direction of the projection is disclosed in U.S. Pat. No. 4,540,367 and the copending application Ser. No. 07/578,396, filed Sep. 7, 1990, which are incorporated herein by reference.

Figure 7:
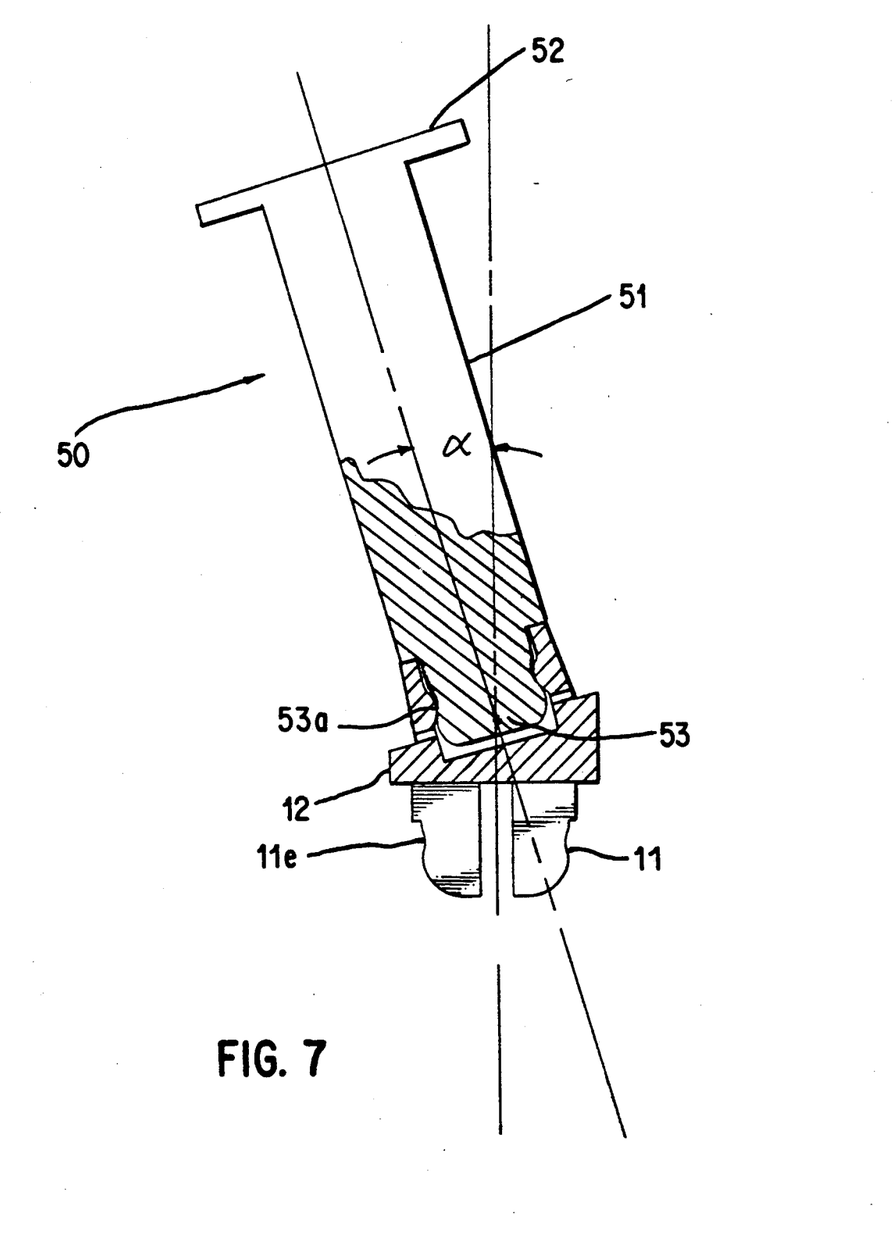
FIG. 7 is a partially cross-sectioned view of the alignment handle seated on the angled support.

To facilitate a visual intra-oral assessment of functional alignment between two or more supports 10 seated in the respective bases 20, an alignment handle 50 is provided. FIG. 7 shows a partial cross-sectional view of the handle. The handle 50 is made from the same plastic material as the cap 40, i.e, nylon and comprises an elongated cylindrical body 51 and enlarged cylindrical flange 52 formed at one end and a projection 53 formed at the opposite end. Specifically, the projection 53 is substantially shaped like the projection 44 formed on the cap 40, and in the similar manner, the projection 53 snaps into the cavity 14 formed in the female eyelet 13. The projection 53 has an hourglass shaped profile as shown clearly in FIG. 7, with a waist portion 53a forming the narrowest point. However, it is to be noted that the projection can be shaped in any conventional manner as long as the projection is held securely in the cavity 14 and maintained with an orientation indicative of the slant α of the female eyelet 13. The enlarged cylindrical disk-like flange 52, located on the opposite end of the projection 53, provides a place for gripping during insertion and removal of the handle from the female eyelet.

The alignment handle 50 serves an important function by sufficiently extending the alignment axis of the angled prosthetic components to allow an accurate visual intra-oral evaluation of the anchor alignment. This is especially important when two or more anchors are used to retain an appliance. All of the anchors must be aligned along the same path to achieve a smooth and non-traumatic insertion and removal of the appliance.

The difficult part of using attachments with implants is providing a parallel alignment of the implant assembly unit with the desirable path of insertion of the dental prothesis retained by the assembly. The present implant assembly unit has a simple and a unique way of attaching and aligning the anchor part of the implant assembly and retaining the dental prothesis. When two or more implants are placed reasonably parallel to each other in the jawbone, all components placed in the implants will be correctly aligned with respect to each other. In this case a conventional 0° one piece anchor can be used. However, in cases where a desirable alignment cannot be achieved by using 0° anchor or if the implants are not parallel, the present 5°, 11° or 17° two piece anchor can be used to achieve the desired alignment.

In operation, after one or more dental implants 30 have been strategically placed flush in the jawbone, and after bone growth has fully integrated the implants in the jawbone, a base 20 with or without a preselected angled support 10 and alignment handle 50 seated therein is screwed into each implant and tightened thereto. If not done previously, a preselected angled support with an alignment handle are seated in each base.

Each angled support 10 is then rotated about the longitudinal axis 2 until a best possible alignment is achieved. By rotating the angled support 10 about its longitudinal axis 2, various offset in any of the 360° direction about the longitudinal axis can be realized, as graphically depicted by the double arrow in FIG. 3.

After visually examining the mutual alignment of the handles 50 snapped in the female eyelets 13 of the anchors, if the handles do not indicate a satisfactory mutual alignment even if the supports are adjusted, differently angled prosthetic supports may be used in various bases 20 to achieve a satisfactory alignment of all anchors with respect to the intended path of insertion of the dental prothesis and to each other.

When the best alignment is achieved, the relative position of the angled support 10 about the base 20 is marked. The base is then unscrewed from the implant in the jaw of the patient. The base and the support are separated, cleaned and then bonded after aligning in the dry environment outside of the mouth of the patient. The preestablished marks are used to capture the prealigned support and base position. Once the bond is set, the threaded shaft of the base is coated with medical-grade silicone adhesive, and the base, with the angled support bonded thereto, is screwed back into the previously set implant in the jaw of the patient. When the base is completely screwed into the implant, the precise threading assures that the anchor will be returned to the exact same position as during the marking step to achieve a correct orientation with the prescribed path of insertion of the dental appliance and with other implant assemblies.

A dental prothesis having one or more teeth is then snapped into one or more female eyelets 13 of the support 10. The dental prothesis includes a male cap at each corresponding female eyelet location. By incorporating this technique, the entire dental prothesis can be removed by the user simply by pulling out the prothesis from the female eyelet(s) and then reinserted again. In many cases, a patient-removable, rather than a permanently cemented prothesis, is more desirable or the only option for restoration of a partially or fully edentulous patient. The above described method facilitates this technique simply and effectively for use with implants. In addition, if a different anchor is required at a later time, perhaps due to the wear, the dental prothesis can be easily removed, and the base 20, which is bonded to the support 10, can be unscrewed from the implant 30. A new base and an appropriately angled support can easily replace the old base and angled support. Using the same (old) implants, new bases and angled supports are aligned as described above.

The foregoing description is only illustrative of the principle of the present invention. It is to be understood that the present invention is not to be limited to the exact construction as illustrated and described herein. Accordingly, all expedient modifications which may be made within the scope and the spirit of the present invention are encompassed herein. For instance, while only one embodiment of the implant type is illustrated for the purpose of simplification, it is to be understood that the present adjustable anchoring system is usable with all implant type having a threaded opening at one end for receiving a threaded portion of the anchor.

I claim:

1. An angularly alignable prosthetic implant attachment system for mounting a dental prosthesis on the jawbone comprising:
   an implant means for permanently mounting to a cavity formed in a jaw bone, said implant means having a bore with a fastening means;

an anchor means having a complementary fastening means for fastening to said bore of said implant means, said anchor means having a seating means;

a prosthesis support means comprising an angled eyelet for coupling with said prosthesis and a coupling means for coupling with said seating means of said anchor means, said angled eyelet being angled at a fixed predetermined angle about a longitudinal axis of said coupling means, wherein said seating means seats said prosthesis support means;

means for rotatably seating said coupling means of said support means so that said coupling means is freely rotatable through 360° about the longitudinal axis of said anchor means so that said support means is alignable about any of the 360° with respect to said anchor means while maintaining said fixed predetermined angle, while said coupling means of said support means is fully seated in said seating means of said anchor means; and means for immobilizing said coupling means relative to said seating means once alignment has been made to prevent said support means from moving relative to said seating means.

2. An angularly alignable prosthesis implant attachment system according to claim 1, wherein said angle of said eyelet is one of 5 degrees, 11 degrees, and 17 degrees.

3. An angularly alignable prosthesis implant attachment system according to claim 1, wherein said angled eyelet forms a female coupling joint having a recess therein.

4. An angularly alignable prosthetic implant attachment system according to claim 3, further comprising a complementary nylon male coupling means which snaps into said eyelet, wherein the prosthesis is formed around said complementary nylon male coupling means.

5. An angularly alignable prosthetic implant attachment system according to claim 4, wherein said complementary nylon male coupling means is removably coupled to said female coupling joint of said eyelet so that the prosthesis can be readily detached from and attached to said eyelet.

6. An angularly alignable prosthesis implant attachment system according to claim 1, wherein said fastening means of said implant means comprises a threaded bore and said complementary fastening means of said anchor means comprises a complementary threaded shaft.

7. An angularly alignable prosthetic implant attachment system according to claim 6, further comprising means for permitting said anchor to be grasped during tightening or loosening of said anchor means to said implant means.

8. An angularly alignable prosthetic implant attachment system according to claim 1, wherein said coupling means of said support means comprises a projection formed in the direction of said longitudinal axis and comprises a cross-shaped slot also formed in the direction of said axis for permitting said projection to deform in a radial direction which is perpendicular to said axis.

9. An angularly alignable prosthesis implant attachment system according to claim 8, wherein said seating means of said anchor means has a complementary recess for seating said projection, said projection snaps into said recess and retains said support means in said anchor means while permitting said support means to freely rotate about said axis.

10. An angularly alignable prosthetic implant attachment system according to claim 1, further comprising an alignment handle for attaching to said angled eyelet for making a visual evaluation of the alignment of said support means.

11. An angularly alignable prosthesis implant attachment system according to claim 10, wherein said alignment handle is snapped into said angled eyelet to facilitate an intra-oral assessment of functional alignment between two or more respective support means.

12. An angularly alignable prosthesis implant attachment system according to claim 10, wherein said alignment handle comprises an elongated cylindrical body having an enlarged disk-like flange formed at one end and a protrusion formed at the opposite end, said protrusion being removably snapped into said eyelet.

13. An angularly alignable prosthesis implant attachment system according to claim 12, wherein said protrusion formed at the opposite end is substantially hourglass shaped in profile.

14. An angularly alignable anchor for a dental prosthesis for use with a dental implant means comprising:

a base anchor means; and a prosthesis support means, wherein said base anchor means comprises a securing portion for removably securing to said implant means and a female coupling means for securing and seating said prosthesis support means;

wherein said prosthesis support means comprises an angled eyelet portion for seating the dental prosthesis and a male coupling means for rotatably coupling with said female coupling means of said anchor means, said angled eyelet portion being angled at a fixed predetermined angle about a longitudinal axis of said male coupling means, means for rotatably seating said male coupling means of said support means to said female coupling means of said anchor means to permit said male coupling means to freely rotate through 360° about the longitudinal axis of said male coupling means, said longitudinal axis being coaxial with a longitudinal aixs of said anchor means so that said prosthesis support means is alignable about nay of the 360+ with respect to said anchor means while maintaining said fixed predetermined angle, while said male coupling means of said support means is fully seated in said female coupling means of said anchor means; and means for immobilizing said male coupling means relative to said female coupling means once alignment has been made to prevent said support means for moving relative to said anchor means.

15. An angularly alignable anchor according to claim 14, wherein said angle of said eyelet portion is one of 5 degrees, 11 degrees, and 17 degrees.

16. An angularly alignable anchor according to claim 14, wherein said angled eyelet portion forms a female coupling joint having a recess therein.

17. An angularly alignable anchor according to claim 16, further comprising a complementary nylon male coupling means which snaps into said eyelet portion, wherein the prosthesis is formed around said complementary nylon male coupling means.

18. An angularly alignable anchor according to claim 17, wherein said complementary male coupling means is removably coupled to said female coupling joint of said eyelet portion so that the prosthesis can be readily detached from and attached to said eyelet portion.

19. An angularly alignable anchor according to claim 14, wherein said securing portion of said anchor means comprises a threaded shaft for securing to said implant means.

20. An angularly alignable anchor according to claim 19, further comprising means for permitting said anchor means to be grasped during tightening or loosening of said anchor means to said implant means.

21. An angularly alignable anchor according to claim 14, wherein said male coupling means of said support means comprises a projection formed in the direction of said longitudinal axis and comprises a cross-shaped slot also formed in the direction of said axis for permitting said projection to deform in a radial direction which is perpendicular to said axis.

22. An angularly alignable anchor according to claim 21, wherein said female coupling means of said anchor means has a complementary recess for seating said projection, said projection snaps into said recess and retains said support means in said anchor means while permitting said support means to freely rotate about said axis.

23. An angularly alignable anchor according to claim 14, further comprising an alignment handle for attaching to said angled eyelet portion for making a visual evaluation of the alignment of said support means.

24. An angularly alignable anchor according to claim 23, wherein said alignment handle is snapped into said eyelet portion to facilitate a visual intra-oral assessment of functional alignment between two or more respective support means.

25. An angularly alignable anchor according to claim 23, wherein said alignment handle comprises an elongated cylindrical body having an enlarged disk-like flange formed at one end and a protrusion formed at the opposite end, said protrusion being removably snapped into said eyelet portion.

26. An angularly alignable anchor according to claim 25, wherein said protrusion formed at the opposite end is substantially hourglass shaped in profile.

27. A method of mounting a dental prosthesis comprising one or more teeth on one or more dental implants into a jawbone, comprising the steps of:
a) inserting one or more dental implants into the jawbone;
b) securing a corresponding number of anchors, one for each implant, each anchor having a female coupling means for securing and seating a prosthesis support into one of said implants;
c) seating a prosthesis support in each said female coupling means, said support having an angled eyelet portion for seating said dental prosthesis and a male coupling means for coupling with each female coupling means of each said anchor, said angled eyelet portion being angled about a longitudinal axis of said male coupling means, wherein said prosthesis support is freely rotatable through 360° about the longitudinal axis of said male coupling means, said longitudinal axis being coaxial with a longitudinal axis of each said anchor so that said prosthesis support is alignable by rotating said prosthesis support while being fully seated in its respective female coupling means;
d) aligning each prosthesis support by rotating said prosthesis support about the longitudinal axis of its respective anchor;
e) marking the position, which indicates a proper alignment, of each support relative to the respective anchor;
f) removing each prosthesis support and anchor from the respective implant;
g) bonding with adhesive each support to the respective anchor using said marking to capture said proper alignment;
h) resecuring each anchor with said support into the respective implant; and
i) attaching said dental prosthesis into the respective supports.

28. A method according to claim 27, wherein said aligning step is carried out by snapping an alignment handle on each angled eyelet portion to facilitate a visual intra-oral assessment of functional alignment between two or more supports.

29. A method according to claim 27, further comprising the steps of replacing each said anchor and the respective support by:
j) removing said dental prosthesis;
k) detaching an anchor and its respective support, which need replacing, together from the respective implant;
l) repeating the steps of b) through i) using a new anchor, and a new support, or a new dental prosthesis, or a combination of a new anchor, a new support and a new dental prosthesis.

30. A method of angularly aligning a support anchor which attaches to a dental implant in a jawbone, comprising the steps of:
a) threading and tightening an anchor into said implant;
b) seating a prosthesis support, which has an angled female eyelet portion, which is angled about a longitudinal axis of the anchor, in said anchor, wherein said prosthesis support is freely rotatable through 360° about the longitudinal axis of said anchor so that said prosthesis support is alignable by rotating said prosthesis support while being fully seated in said anchor;
c) aligning said support relative to said anchor by rotating said support about said axis while said support is seated in said anchor;
d) marking the relative position of said anchor and said support which is indicative of the alignment;
e) removing said support and said anchor from said implant;
f) bonding said support to said anchor using said marking to capture the alignment;
g) rethreading the bonded anchor and support into said implant, the threading assuring said anchor to return to the exact same position as during the marking step; and
h) attaching a dental prosthesis.

31. A method according to claim 30, wherein said aligning step is carried out by snapping an alignment handle on said angled eyelet portion to facilitate a visual inta-oral assessment of functional alignment between two or more supports.

32. A method according to claim 30, further comprising the steps of replacing said anchor and said support by:
i) removing said dental prosthesis;
j) detaching said anchor and said support together from said implant;
k) repeating the steps of a) through h) using a new anchor, a new support, or a new dental prosthesis, or a combination of a new anchor, a new support, and new dental prosthesis.

* * * * *